United States Patent
Nishimura et al.

(10) Patent No.: US 7,275,862 B2
(45) Date of Patent: Oct. 2, 2007

(54) DIFFERENTIAL SCANNING CALORIMETER WITH A SECOND HEATER

(75) Inventors: Shinya Nishimura, Chiba (JP); Rintaro Nakatani, Chiba (JP); Ryoichi Kinoshita, Chiba (JP)

(73) Assignee: SII NanoTechnology Inc. (JP)

( * ) Notice: Subject to any disclaimer, the term of this patent is extended or adjusted under 35 U.S.C. 154(b) by 55 days.

(21) Appl. No.: 10/990,636

(22) Filed: Nov. 17, 2004

(65) Prior Publication Data
US 2005/0163188 A1 Jul. 28, 2005

(30) Foreign Application Priority Data
Nov. 18, 2003 (JP) .............................. 2003-387731

(51) Int. Cl.
*G01K 17/08* (2006.01)
*G01N 25/20* (2006.01)
(52) U.S. Cl. ...................... 374/11; 374/1 D; 374/31
(58) Field of Classification Search ................. 374/10, 374/11, 29, 31, 33, 12, 32, 34–40; 422/51; 436/147
See application file for complete search history.

(56) References Cited

U.S. PATENT DOCUMENTS

| | | | | |
|---|---|---|---|---|
| 2,800,793 A * | 7/1957 | Oliver | ........................ | 374/33 |
| 3,365,944 A * | 1/1968 | Hoagland et al. | ............. | 374/34 |
| 3,491,581 A * | 1/1970 | Harlan et al. | .................. | 374/12 |
| 4,783,174 A * | 11/1988 | Gmelin et al. | ................ | 374/33 |
| 5,439,291 A * | 8/1995 | Reading | ....................... | 374/11 |
| 5,547,282 A * | 8/1996 | Pinhack et al. | ............... | 374/36 |
| 5,711,604 A * | 1/1998 | Nakamura | .................... | 374/44 |
| 6,390,669 B1 * | 5/2002 | Nakamura et al. | ............ | 374/12 |
| 6,422,742 B1 * | 7/2002 | Kinoshita | .................... | 374/10 |
| 6,488,406 B2 * | 12/2002 | Danley | ........................ | 374/10 |
| 6,523,998 B1 * | 2/2003 | Danley et al. | ................ | 374/12 |
| 6,530,686 B1 * | 3/2003 | Nakamura | .................... | 374/11 |
| 6,583,391 B2 * | 6/2003 | Jorimann et al. | ........... | 219/497 |
| 6,913,383 B2 * | 7/2005 | Jorimann et al. | ............. | 374/31 |
| 2001/0038660 A1 * | 11/2001 | Nagasawa | .................... | 374/11 |
| 2003/0026319 A1 * | 2/2003 | Kinoshita | .................... | 374/31 |
| 2005/0190813 A1 * | 9/2005 | Schick | ........................ | 374/10 |

* cited by examiner

*Primary Examiner*—Gail Verbitsky
(74) *Attorney, Agent, or Firm*—Adams & Wilks

(57) ABSTRACT

A differential scanning calorimeter has a heat sink for accommodating therein a measurement sample and a reference material, and a differential heat flow detector that detects a temperature difference between the sample and the reference material. A cooling mechanism cools the heat sink, and a thermoconductor is disposed between the cooling mechanism and the heat sink and forms a heat flow path between the two. A first heater heats the heat sink, and a second heater heats the thermoconductor to thereby heat the heat sink. The second heater begins operating before the first heater nears its rated maximum output power.

7 Claims, 2 Drawing Sheets

DIFFERENTIAL SCANNING CALORIMETER WITH A SECOND HEATER

BACKGROUND OF THE INVENTION

The present invention relates to a differential scanning calorimeter for a thermal analyzer.

A differential scanning calorimeter of a thermal analyzer is equipped with a heat-controlled heat sink, a sample within the heat sink, a reference material holder, a heater for heating the heat sink, and a cooling device for cooling the heat sink. With differential scanning calorimeters of the related art, a cooling device comes into direct contact with a heat sink so as to cool the heat sink. Cooling devices taking liquid nitrogen as a medium are disclosed in Japanese issued Patent Tokkohei 2-116744 and Japanese issued Patent Tokkohei 7-122619. At the cooling device, an electrical cooling device that compresses a cooling agent using a compressor so as to cause adiabatic expansion that in turn produces cooling is provided. A metallic member connected to the electrical cooling device then makes direct contact with a heat sink so as to cause cooling.

With heat-flux differential scanning calorimeters of the related art, it is preferable for providing power to the heater that heats the heat sink to be of high-resolution in order to control the temperature of the heat sink as precisely as possible. For example, with differential scanning calorimeters with an upper limit of 750° C., an ideal maximum heater power is taken to be a value sufficient for requiring heating necessary to bring the heat sink temperature up to 750° C.

Differential scanning calorimeters are connected to a device for cooling a heatsink such as an electrical cooling device that compresses a cooling medium using, for example, a compressor so as to bring about adiabatic expansion which in turn brings about cooling in order to measure negative temperature bands or measure falling temperatures. However, with differential scanning calorimeters designed with the sufficient heating power necessary for heating processing, in cases where a cooling device is not connected, it is possible for the temperature to be increased up to 750° C. but when an electrical cooling device is connected, the current for heating the heat sink flows in the cooling mechanism, and because extra heater power is therefore required, heating up to 750° C. cannot be achieved for the differential scanning calorimeter and the temperature range that can be measured is therefore reduced. Further, when a cooling device is installed and the outputted heater power is increased to achieve heating up to 750° C., the resolution of the control of the heater power deteriorates, and heat sink temperature can no longer be controlled in a precise manner.

In order to resolve the aforementioned problems, the current application sets out to precisely control heat sink temperature using high-resolution heater power without reducing the measurable temperature range of a differential scanning calorimeter to which an electrical cooling device for cooling a heat sink is connected.

SUMMARY OF THE INVENTION

In order to resolve the aforementioned problems, in the invention of this application, a differential scanning calorimeter has a heatsink for housing a measurement sample and a reference material, a first heater for heating the heatsink, and a differential heat flow detector fixed to a bottom plate of the heatsink. A cooling mechanism is provided for cooling the heatsink, and a thermoconductor equipped with a second heater is disposed between the heatsink and the cooling mechanism so that a heat path is then formed between the heatsink and the cooling mechanism by the thermoconductor.

The second heater is fixed to the thermoconductor. The supply of heater power to the second heater is outputted using a preset heater power table according to the temperature and heating speed of the temperature program rather than according to feedback control. When the heatsink is heated up with the cooling mechanism put into a sufficiently cooled state by the cooling device, surplus power resulting from heat flowing into the cooling mechanism from the heatsink is supplemented by the power of the second heater and surplus power in the control of the first heater is not consumed so that an upper limit measuring temperature is maintained. As a result, it is difficult for heat to flow to the cooling mechanism from the heatsink and the power required for the first heater to increase the temperature of the heatsink is not remarkably larger.

DETAILED DESCRIPTION OF THE PREFERRED EMBODIMENT

Figure 1:
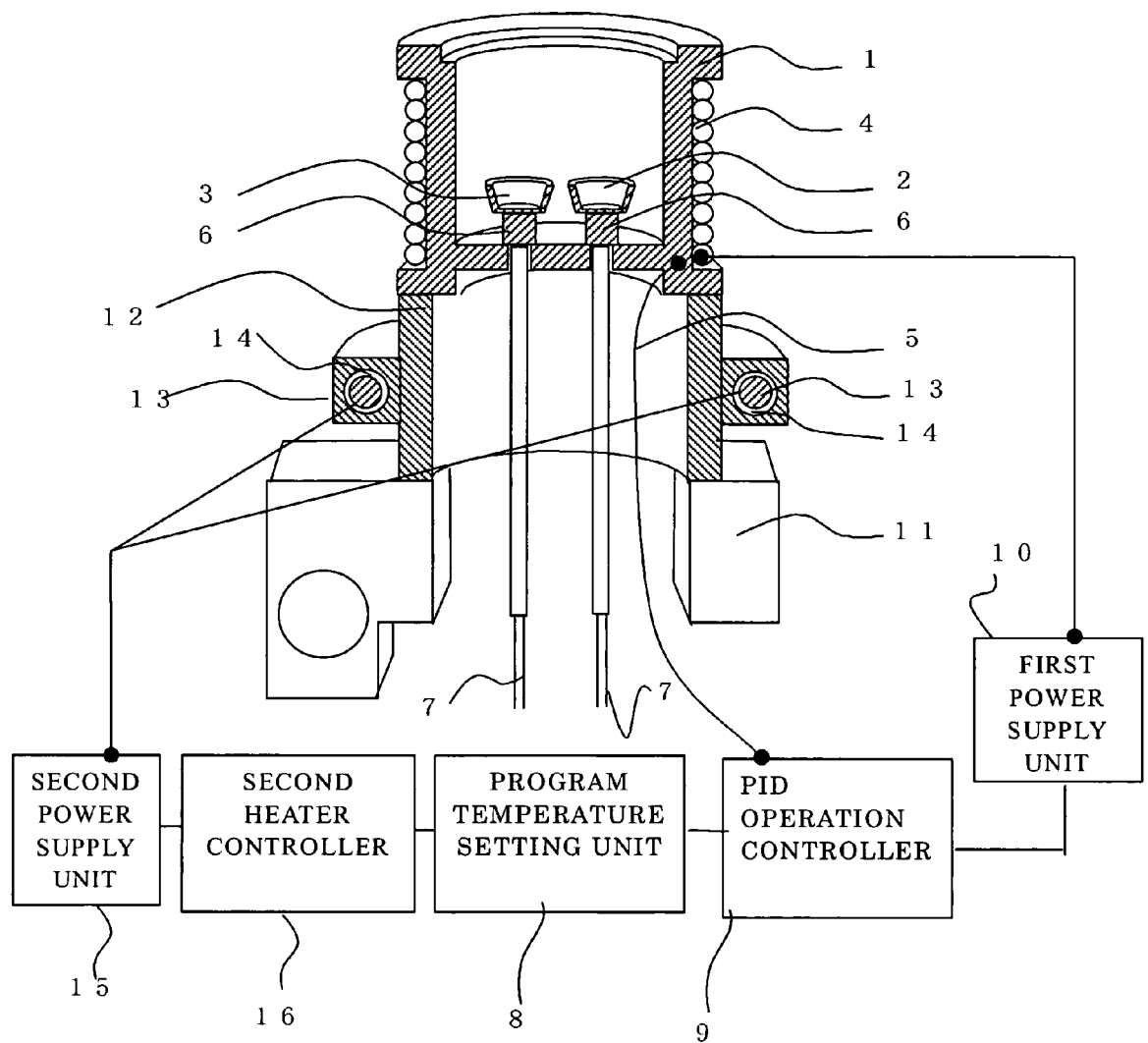
FIG. 1 is a cross-sectional view of a differential scanning calorimeter.

A description is now given using FIG. 1 of a differential scanning calorimeter equipped with a second heater of the present invention. A sample holder 2 and a reference material holder 3 are provided within a chamber inside the heat sink 1. A first heater 4, with an insulation film, for heating the heat sink 1 and a heat control electrode 5 for detecting heat sink temperature and producing a temperature detection signal for controlling feedback are provided on a side surface of the heat sink 1.

A differential heat flow detector 6 is provided between a bottom plate of the heat sink 1, and the sample holder 2 and reference material holder 3. Thermocouple elements 7 are then welded to the differential heat flow detector 6 and a temperature difference between the sample and the reference material is detected. The temperature difference signal is outputted as a heat flow difference signal flowing into the sample side and the reference material side.

An arbitrary temperature program decided by a measurer is input to a temperature program setting unit 8, and temperature signals set by programs from the temperature program setting unit 8 are outputted. A PID operation controller 9 carries out a PID operation from a difference between a temperature signal outputted by the heat control electrode 5 and a temperature signal from the temperature program setting unit 8 so as to provide an appropriate heater power output to the first heater 4 via a first power supply unit 10. In this way, the heat sink controls temperature in a precise manner using a feedback loop of the PID operation.

Next, a description is given of a thermoconductor and cooling mechanism the second heater is provided with. A cooling mechanism 11 for cooling the heatsink 1, a thermoconductor 12 forming a heat path between the heatsink 1 and the cooling mechanism 11 and a second heater 13 for heating the thermoconductor 12 are also provided. The thermoconductor 12 is such that the heat sink 1 and the cooling mechanism 11 are fastened with screws and soldered using metal, so as to form a heat path between the heat sink and the cooling mechanism. A second heater 13 is inserted into a second heater insertion hole 14 provided at the thermoconductor 12.

A second power supply 15 is connected to the second heater 13. The temperature signal from the program temperature setting unit 8 is outputted to a second heater control unit 16 and setting is performed so that power is supplied to the second heater as shown in equation (1).

$$P = \alpha(T_p) + \beta \frac{dT_p}{dt} \quad (1)$$

Figure 2:
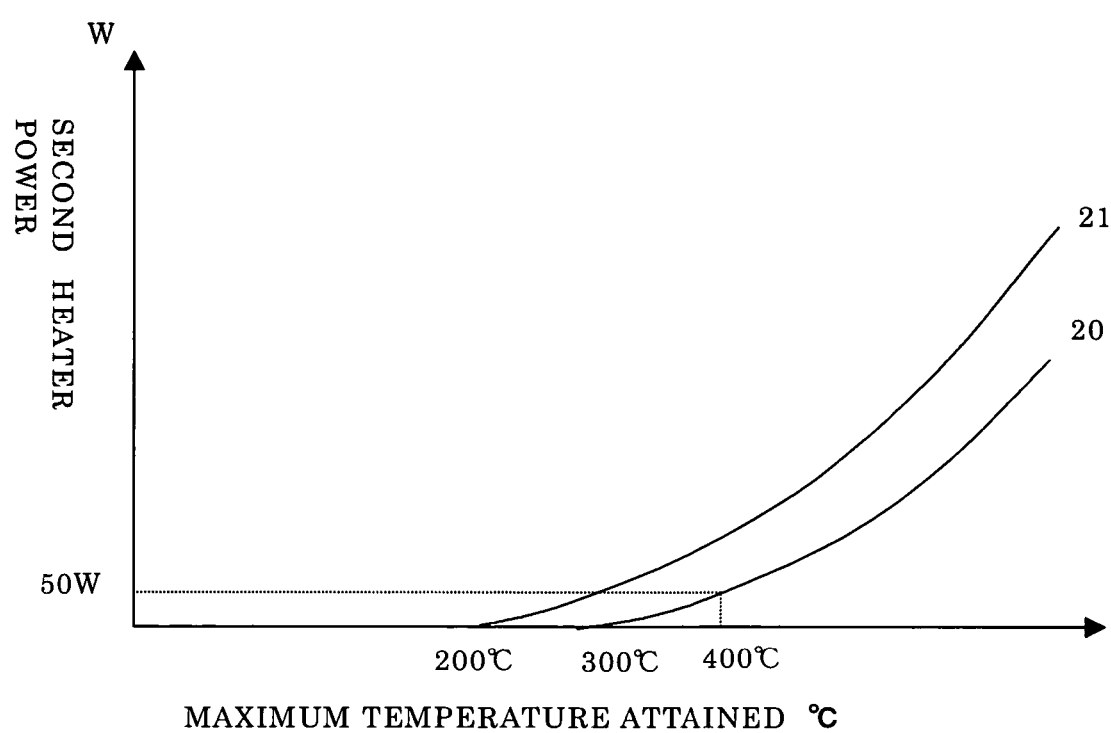
FIG. 2 is a power supply table for a second heater.

P: supplied power
Tp: program temperature decided by measurer
α: supplied power coefficient for the program temperature
t: time
dTp/dt: program temperature change speed
β: constant The supplied power coefficient α(Tp) is then set in advance through experimentation. With a differential scanning calorimeter installed with a cooling device for cooling at a fixed power and with a first heater operating at a prescribed program temperature, a fixed power of, for example, 50 W is supplied to the second heater 13, temperature is increased at 20° C./min, and a maximum sample temperature reached at this time of, for example, 400° C. is read out. Next, in a similar method, respective maximum temperatures attained by the sample when the power provided to the second heater is sequentially changed are read out, with a graph showing the relationship between the second heater power and the maximum sample temperature attained being shown in FIG. 2. The graph at this time becomes as in graph 20. The maximum temperature attained by the sample when the second heater is zero is 300° C., and a second heater is required for making the temperature greater than 300° C.

When supply of power to the second heater satisfies the graph 20, in a temperature band above 300° C. where supply of power to the second heater commences, the power for the first heater is a maximum value, and the power for the second heater is also at a minimum limit required for maximum temperature attainment. Feedback control for the power for the first heater therefore does not function at the point of the maximum temperature attained.

All of the functions in the graph 20 for the second heater power value all move in parallel, and graph 21 is provided so that so as to start supply of power from 200° C. By performing setting in this manner, in a temperature band of 200° C. or less, temperature control is carried out in a state where only the first heater is operating, and at the time of a temperature of over 200° C. or more, operation can be achieved in such a manner that the power of the first heater does not become the maximum value as a result of causing the second heater power to operate and feedback control of the power of the first heater can be controlled. Further, it is also possible for the output of the second heater to be increased by the speed of the rise in temperature as a result of the presence of the coefficient β of the second term of equation 1. In the process for the rapid temperature rise program, the value for the second heater power is increased so that the rising temperature performance is increased, while with the low speed temperature rise process it is possible to perform ideal control to temperature rises and cooling by keeping temperature rise performance low. Further, the second heater power does not carry out feedback control. The thermoconductor 12 heated by the second heater 13 therefore does not swing with respect to temperature. This therefore does not become a cause of fluctuations in the temperature of the heatsink.

By providing a differential scanning calorimeter of the present invention with a thermoconductor provided with a second heater between a heatsink temperature-controlled by a first heater and a cooling mechanism, it is possible to ensure that a measurable temperature range is not reduced by supplementing excess power for causing heat to flow to the cooling mechanism from the heatsink with an electrical cooling device in an installed state to be supplemented with power of a second heater. Further, the power for the first heater may be of a sufficient value necessary for an upper temperature limit of the differential scanning calorimeter. This makes high-resolution feedback control possible and means that it is possible to precisely control heatsink temperature.

What is claimed is:

1. A differential scanning calorimeter comprising: a heat sink for. housing a measurement sample and a reference material; a first heater for heating the heat sink; a differential heat flow detector fixed to a bottom plate of the heat sink for detecting a temperature difference between the sample and the reference material; a cooling mechanism for cooling the heat sink; a thermoconductor disposed between the heat sink and the cooling mechanism and forming a heat flow path between the heat sink and the cooling mechanism; and a second heater disposed outside the heat sink for heating the thermoconductor.

2. A differential scanning calorimeter according to claim 1; wherein power of the second heater is decided in advance according to the temperature of the heat sink and heating speed.

3. A differential scanning calorimeter according to claim 1; further including means for increasing the output power of the second heater.

4. A differential scanning calorimeter according to claim 1; wherein the second heater operates within a temperature range where feedback control of the first heater is possible, and operates before a maximum attainable temperature possible using the first heater is reached.

5. A differential scanning calorimeter according to claim 1; wherein the thermoconductor has a ring-shaped structure having a second heater insertion opening, the second heater being attachable in and detachable from the insertion opening.

6. A differential scanning calorimeter according to claim 2; wherein the thermoconductor has a ring-shaped structure having a second heater insertion opening, the second heater being attachable in and detachable from the insertion opening.

7. A differential scanning calorimeter according to claim 1; wherein the second heater operates before the power of the first heater becomes a maximum value and provides power decided in advance according to a temperature program of the heat sink.

* * * * *